United States Patent
Crabtree et al.

(10) Patent No.: US 7,220,552 B1
(45) Date of Patent: *May 22, 2007

(54) BIFUNCTIONAL MOLECULES AND THEIR USE IN THE DISRUPTION OF PROTEIN-PROTEIN INTERACTIONS

(75) Inventors: Gerald R. Crabtree, Woodside, CA (US); Kryn Stankunas, Menlo Park, CA (US); Roger Briesewitz, Mountain View, CA (US); Thomas J. Wandless, Stanford, CA (US)

(73) Assignee: The Board of Trustees of the Leland Stanford Junior University, Palo Alto, CA (US)

(*) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 09/716,054

(22) Filed: Nov. 17, 2000

Related U.S. Application Data

(60) Provisional application No. 60/166,674, filed on Nov. 19, 1999.

(51) Int. Cl.
*G01N 33/53* (2006.01)
*A61K 39/00* (2006.01)

(52) U.S. Cl. .................. 435/7.1; 435/7.8; 435/69.1; 435/69.2; 424/136.1; 424/193.1; 530/362; 530/380; 530/385

(58) Field of Classification Search .......... 424/136.1, 424/193.1, 133.1, 153.1, 173.1, 175.1; 530/362, 530/380, 385, 350, 402, 413, 324, 856; 435/69.2, 435/78, 69.1, 233, 214, 69.6, 320.1, 172.3, 435/252.33, 7.1
See application file for complete search history.

(56) References Cited

U.S. PATENT DOCUMENTS

| 5,242,810 A * | 9/1993 | Maraganore et al. ...... 435/69.2 |
| 5,382,657 A | 1/1995 | Karasiewicz et al. |
| 5,457,182 A * | 10/1995 | Wiederrecht et al. ....... 530/402 |
| 5,830,462 A | 11/1998 | Crabtree et al. |
| 5,834,266 A | 11/1998 | Crabtree et al. |
| 5,840,733 A | 11/1998 | Krantz et al. |
| 5,843,440 A | 12/1998 | Pouletty et al. |
| 5,869,337 A | 2/1999 | Crabtree et al. |
| 5,871,753 A | 2/1999 | Crabtree et al. |
| 6,670,348 B1 | 12/2003 | Rosen et al. |
| 2002/0045570 A1 | 4/2002 | Rosen et al. |

FOREIGN PATENT DOCUMENTS

| WO | WO 91/01743 | 2/1991 |
| WO | WO 94/18317 | 8/1994 |
| WO | WO 95/02684 | 1/1995 |
| WO | WO 95/05389 | 2/1995 |
| WO | WO 95/10302 | 4/1995 |
| WO | WO-95/10302 A1 * | 4/1995 |
| WO | WO 96/06111 | 2/1996 |
| WO | WO 96/12796 | 5/1996 |
| WO | WO 96/13613 | 5/1996 |
| WO | WO 97/25074 | 7/1997 |
| WO | WO 97/29372 | 8/1997 |
| WO | WO 98/00171 | 1/1998 |
| WO | WO 98/11437 | 3/1998 |
| WO | WO 98/46270 | 10/1998 |
| WO | WO 98/47002 | 10/1998 |
| WO | WO 98/47916 | 10/1998 |
| WO | WO 99/61055 | 12/1999 |

OTHER PUBLICATIONS

Griffith et al., X-ray structure of calcineurin inhibition by the immunophilin-immunosuppressant FKBP12-FK506 complex., Cell, vol. 82., pp. 507-522, Aug. 11, 1995.*
Varshavsky., Codiminant interference, antieffects, and multitargets drugs, Proc. Natl. Acad. Sci. USA, vol. 95, pp. 2094-2099, 1998.*
Jein et al., J Med Chem., 1994, 37, 2100-2105.*
Kuduk et al. Bio & Med Chemistry Letters, 10, 2000, 1303-1306.*
Waldmann, Science, vol. 252, Jun. 21, 1991, pp. 1657-1662.*
Tockman et al. Cancer Research 52:2711s-2718s, 1992.*
Peipp and Valerius, Biochemistry Society Transactions, 2002, vol. 30, part 4, pp. 507-511.*
Ivery (Medicinal Research reviews, 2000, 20(6), 452-484).*
Al-Obeidi, et al., (1990) "Synthesis and Actions of a Melanotropin Conjugate, Ac-[Nle$^4$, Glu(gamma-4'-hydroxyanilide)$^5$, D-Phe$^7$]α - MSH$_{4\times10}$ -NH$_2$, on Melanocytes and Melanoma Cells In Vitro," *Journal of Pharmaceutical Sciences* vol. 79, No. (6):500-504.
Atwell, John L., et al., (1996) "Design and Expression of a Stable Bispecific scFv Dimer With Affinity for Both Glycophorin and N9 Neuraminidase," *Molecular Immunology* vol. 22, No. (17/18):1301-1312.
Belshaw, et al., (1996) "Controlling Protein Association and Subcellular Localization with a Synthetic Ligand that Induces Heterodimerization of Proteins," *Proc. Natl. Acad. Sci. U.S.A.* vol. 93:4604-4607.

(Continued)

*Primary Examiner*—Long V. Le
*Assistant Examiner*—Lisa V. Cook
(74) *Attorney, Agent, or Firm*—Bret E. Field, Esq.; Bozicevic, Field & Francis LLP

(57) ABSTRACT

Bifunctional inhibitor molecules and methods for their use in the inhibition of protein—protein interactions are provided. The subject bifunctional inhibitor molecules are conjugates of a target protein ligand and a blocking protein ligand, where these two moieties are optionally joined by a linking group. In the subject methods, an effective amount of the bifunctional inhibitor molecule is administered to a host in which the inhibition of a protein—protein interaction is desired. The bifunctional inhibitor molecule simultaneously binds to its corresponding target and blocking proteins to produce a tripartite complex that inhibits the target protein—protein interaction. The subject methods and compositions find use in a variety of applications, including therapeutic applications.

17 Claims, 4 Drawing Sheets

OTHER PUBLICATIONS

Bernstein, Kenneth E., et al., (1990) "A Deeply Recessed Active Site in Angiotensin-Converting Enzyme Is Indicated From the Binding Characteristics of Biotin-Spacer-Inhibitor Reagents," *Biochemical and Biophysical Communications* vol. 167, No. (1):310-316.

Bourdouxhe-Housiaux, Catherine, et al., (1996) "Interaction of DNA-Threading Peptide-Amsacrine Conjugates With DNA and Chromatin," *Anti-Cancer Drug Design* vol. 11:509-525.

Brochu, et al., (1992) "Modes of Action and Inhibitory Activities of New Siderophore-β-Lactam Conjugates that use Specific Iron Uptake Pathways for Entry into Bacteria," *Antimicrobial Agents and Chemotherapy* vol. 36, No. (10):2166-2175.

Briesewitz, et al., (1999) "Affinity Modulation of Small-Molecule Ligands by Borrowing Endogenous Protein Surfaces," *P.N.A.S* vol. 96, No. (5):1953-1958.

Chakraborty, TK., et al., (1995) "Design and Synthesis of a Rapamycin-Based High Affinity Binding FKBP12 Ligand," *Chemistry & Biology* vol. 2:157-161.

Crabtree, Gerald R., et al., (1996) "Three-Part Inventions: Intracellular Signalling and Induced Proximity," *Elsevier Trends Journal* pp. 418-422.

Heath, et al., (1986) "Liposome-Mediated Delivery of Pteridine Antifolates to cells in Vitro: Potency of Methotrexate, and its α and γ Substituents," *Biochimica et Biophysica Acta* vol. 862:72-80.

Holt, et al., (1994) "Structure-Activity Studies of Synthetic FKBP Ligands as Peptidyl-Prolyl Isomerase Inhibitors," *Bioorganic and Medicinal Chemistry Letters* vol. 4, No. (2):315-320.

Kramer, Werner, et al., (1992) "Liver-Specific Drug Targeting by Coupling to Bile Acids," *The Journal of Biological Chemistry*, vol. 267, No. (2):18598-18604.

Luengo, et al., (1994) "Synthesis and Structure-Activity Relationships of Macrocyclic FKBP Ligands," *Bioorganic and Medicinal Chemistry Letters* vol. 4, No. (2):321-324.

Lussow, et al., (1996) "Targeting of Antihapten Antibodies to Activated T Cells via an IL-2-Hapten Conjugate Prolongs Cardio Graft Survival," *Trasplantation* vol. 62, No. (12):1703-1708.

Maeda, et al., (1997) "Amino Acids and Peptides XXXII: A Biofunctional Poly(Ethylene Glycol) Hybrid of Fibronectin-Related Peptides," *Biochemical and Biophysical Research Communications* vol. 241:595-598.

Mogre, R.M., et al., (1987) "A New Carbene Based Heterbifunctional Reagent: Photochemical Crosslinking of Aldolase," *FEBS Letters*, vol. 221, No. (2):408-414.

Mu, Yu., et al., (1999) "Bioconjugation of Laminin Peptide YIGSR With Poly(Styrene Co-Maleic Acid) Increases Its Antimetastatic Effect on Lung Metastasis of B16-BL6 Melanoma Cells," *Biochemical and Biophysical Research Communications*, vol. 255:75-79.

Varshavsky, Alexander, (1998) "Codominant Interference, Antieffectors, and Multitarget Drugs," *Proc. Natl. Acad. Sci. USA*, vol. 95:2094-2099.

Varshavsky, Alexander, (1995) "Codominance and Toxins: A Path to Drugs of Neatly Unlimited Selectivity," *Proc. Natl. Acad. Sci. USA*, vol. 92:3663-3667.

Zunino, et al., (1984) "Compassion of Antitumor Effects of Daunorubicin Covalently Linked to Poly-L-Amino Acid Carriers," *Eur. J. Cancer Chem. Oncol.* vol. 20, No. (3):421-425.

Choi et al. (1996) "Structure of the FKBP12-Rapamycin Complex Interacting with the Binding Domain of Human FRAP." *Science*, vol. 273:239-242.

Clardy (1999) "Borrowing to make ends meet." *Proc. Natl. Acad. Sci. USA*, vol. 96:1826-1827.

Garboczi et al. (1996) "Structure of the complex between human T-cell receptor, viral peptide and HLA-A2." *Nature*, vol. 384:134-141.

Griffith et al. (1995) "X-Ray Structure of Calcineurin Inhibited by the Immunophilin-Immunosuppressent FKBP12-FK506 Complex." *Cell*, vol. 82:507-522.

Johnson et al. (1997) "Amino-terminal dimerization of an erythropoietin mimetic peptide results in increased erythropoietic activity." *Chemistry & Biology*, vol. 4:939-950.

Kissenger et al. (1995) "Crystal structures of human calcineurin and the human FKBP12-FK506-calcineurin complex." *Nature*, vol. 378:641-644.

Klemm et al. (1997) "Rapid targeting of nuclear proteins to the cytoplasm" *Current Biology*, vol. 7:638-644.

Livnah et al. (1996) "Functional Mimicry of a Protein Hormone by a Peptide Agonist: The EPO Receptor Complex at 2.8Å" *Science*, vol. 273:464-471.

Riviera et al. (1996) "A humanized system for pharmacologic control of gene expression." *Nature Medicine*, vol. 2(9):1028-1032.

Spencer et al. (1993) "Controlling Signal Transduction with Synthetic Ligands." *Science*, vol. 262:1019-1024.

Spencer et al. (1996) "Functional analysis of Fas signaling in vivo using synthetic inducers of dimerization." *Current Biology*, vol. 6(7):839-847.

Jain et al. (2000) "Protein Surface Recognition by Synthetic Receptors Based on a Tetraphenylporphyrin Scaffold." *Organic Letters*, vol. 2(12):1721-1723.

Li et al. (1997) "A computer screening approach to immunoglobulin superfamily structures and interactions: Discovery of small non-peptidic CD4 inhibitors as novel immunotherapeutics." *Proc. Natl. Acad. Sci. USA*, vol. 94:73-78.

Park et al. (1999) "Protein Surface, Recognition by Synthetic Receptors: A Route to Novel Submicromolar Inhibitors for α-Chymotrypsin." *J. Am. Chem. Soc.*, vol. 121:8-13.

Regan et al. (1997) "Anionic- and Lipophilic-Mediated Surface Binding Inhibitors of Human Leukocyte Elastase." *J. Med. Chem.*, vol. 40:3408-3422.

Tilley et al. (1997) "Identification of a Small Molecule Inhibitor of the IL-2/IL-2Rα Receptor Interaction Which Binds to IL-2." *J. Am. Chem. Soc.*, vol. 119:7589-7590.

Kuduk et al. "Synthesis and Evaluation of Geldanamycin-Testosterone Hybrids" Bioorg. Med. Chem. Lett. 10 (2000) 1305-1306.

* cited by examiner

The mode of action of blocking antibodies can be recapitulated with small molecules NFAT translocates into the nucleus after activation of clacineurin with ionomycin

US 7,220,552 B1

BIFUNCTIONAL MOLECULES AND THEIR USE IN THE DISRUPTION OF PROTEIN-PROTEIN INTERACTIONS

CROSS REFERENCE TO RELATED APPLICATIONS

Pursuant to 35 U.S.C. § 119 (e), this application claims priority to the filing date of the U.S. Provisional Patent Application Ser. No. 60/166,675 filed Nov. 19, 1999, the disclosure of which is herein incorporated by reference.

ACKNOWLEDGMENT

This invention was made with United States Government support under Grant No. CA39612 awarded by National Institutes of Health. The United States Government has certain rights in this invention.

INTRODUCTION

1. Technical Field

The field of this invention is pharmacology.

2. Background of the Invention

The inhibition or activation of biological processes with drugs that act as antagonists or agonists is the basis of the chemotherapy of diseases. For a small molecule to interact with high affinity and specificity with a given protein target requires that the molecule is able to establish a sufficient number of molecular interactions which will provide the required free energy of binding. If the active site of a protein is a deep pocket, small molecule drugs can take advantage of interactions that can be established on all sides of the molecule. However, if the active site of a protein target is relatively flat, the contacts a small molecule can establish may be limited to one face. As a result, the affinity of the small molecule for the target may not be very high.

The active site or the target site of many potential drug targets is relatively flat. Usually, these sites are not catalytically active but instead they are used to bind to other proteins. The interface of such protein—protein interactions can be rather large and may involve contacts between 20 or 30 amino acids on both proteins. Due to the flat surface small molecules often cannot establish the number of contacts required for a high affinity binding event that can compete with the binding of the large protein ligand to the target. It is considered an intractable problem to develop small molecules that can disrupt such protein—protein interactions.

As such, the development of a technique that would allow the disruption of protein—protein interactions, particularly through use of a small molecule therapeutic agent, is of particular interest.

RELEVANT LITERATURE

Patent publications of interest include: WO 91/01743; WO 94/18317; WO 95/02684; WO 95/10302; WO 96/06111; WO 96/12796; WO 96/13613; WO 97/25074; WO 97/29372; WO 98/11437; WO 98/47916; U.S. Pat. No. 5,830,462; U.S. Pat. No. 5,843,440; and U.S. Pat. No. 5,871,753. References of interest include: Briesewitz et al., Proc. Nat'l Acad. Sci. USA (March 1999) 96: 1953–1958; Clardy, Proc. Nat'l Acad. Sci. USA (March 1999) 1826–1827; Crabtree & Schreiber, Elsevier Trends Journal (November 1996) 418–422; Spencer et al., Curr. Biol. (July 1996) 6:839–847; Spencer et al., Science (1993) 262: 1019; Chakraborty et al., Chem. & Biol. (March 1995) 2:157–161; Ho et al., Nature (1996) 382: 822; Riviera et al., Nature Medicine (1996) 2: 1028; Klemm et al., Current Biology (1997) 7: 638; Belshaw et al., Proc. Nat'l. Acad. Sci. USA (1996) 93: 4604; Livnah et al., Science (1996) 273: 464; Johnson et al., Chemistry and Biology, (1997) 4: 939; Garboczi et al., Nature (1996) 384:134; Kissenger et al., Nature (1995) 378:641; Griffith et al., Cell (1995) 82: 507; Choi et al., Science (1996) 273:239. Also of interest are Kramer et al., J. Biol. Chem. (1992) 267:18598–18604; and Varshavsky, Proc. Nat'l Acad. Sci. USA (March 1998) 95: 2094–2099; Varshavsky, Proc. Nat'l Acad. Sci. USA (April 1995) 92:3663–3667; and Mu et al., Biochem. Biophys. Res. Comm. (1999) 255:75–79.

SUMMARY OF THE INVENTION

Bifunctional inhibitor molecules and methods for their use in the inhibition of protein—protein interactions are provided. The subject bifunctional inhibitor molecules are conjugates of a target protein ligand and a blocking protein ligand, where these two moieties are optionally joined by a linking group. In the subject methods, an effective amount of the bifunctional inhibitor molecule is administered to a host in which the inhibition of a protein—protein interaction is desired. The bifunctional inhibitor molecule simultaneously binds to its corresponding target and blocking proteins to produce a tripartite complex that inhibits the target protein—protein interaction between the target protein and a second binding protein. The subject methods and compositions find use in a variety of applications, including therapeutic applications.

DESCRIPTION OF THE SPECIFIC EMBODIMENTS

Bifunctional inhibitor molecules and methods for their use in the inhibition of protein—protein interactions between a target protein and a second binding protein are provided. The subject bifunctional inhibitor molecules are conjugates of a target protein ligand and a blocking protein ligand, where these two moieties are optionally joined by a linking group. In the subject methods, an effective amount of the bifunctional inhibitor molecule is administered to a host in which the inhibition of a protein—protein interaction is desired. The bifunctional inhibitor molecule simultaneously binds to its corresponding target and blocking proteins to produce a tripartite complex that inhibits the target protein—protein interaction. The subject methods and compositions find use in a variety of applications, including therapeutic applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Bifunctional Molecule

Figure 1:
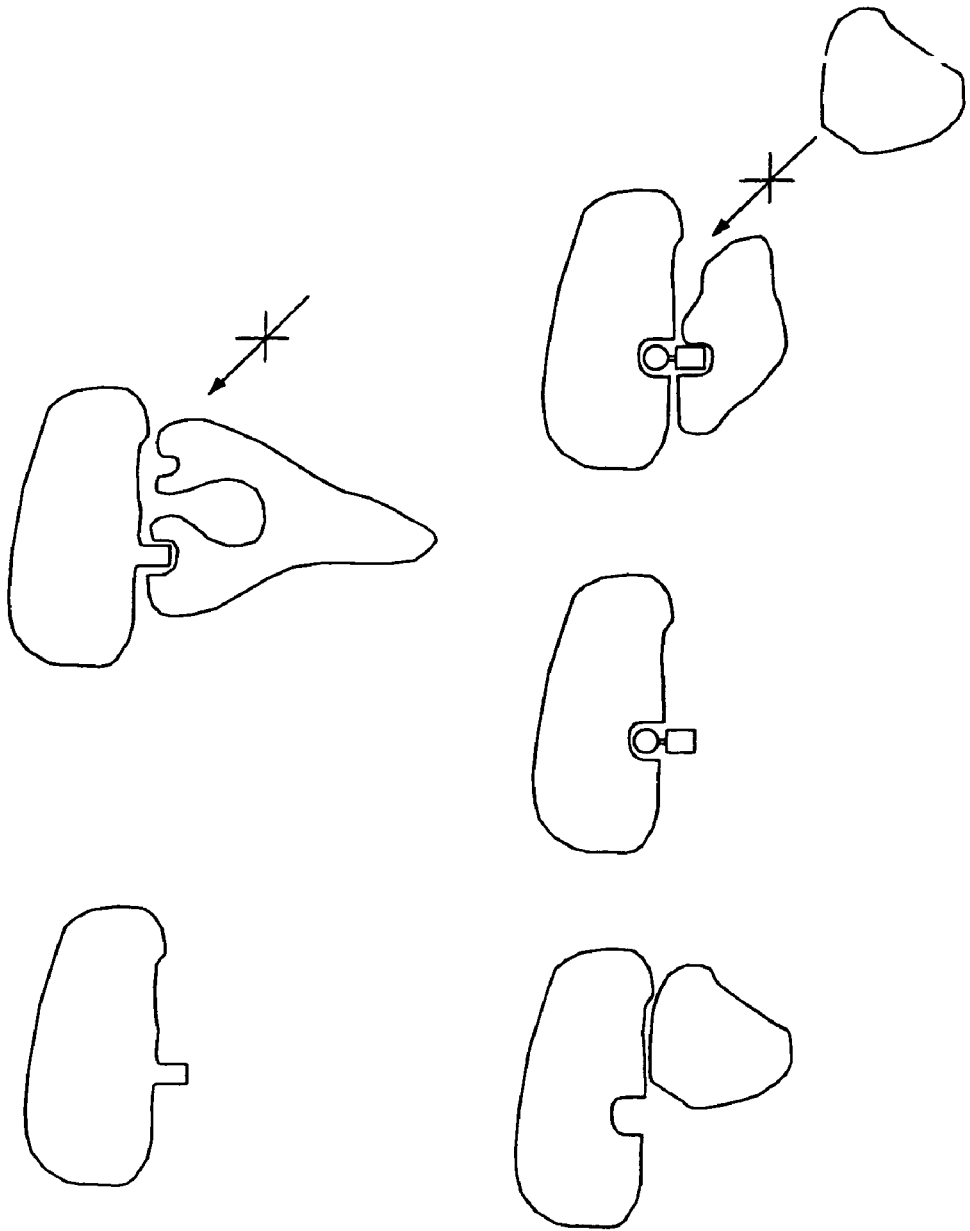
FIG. 1 provides a schematic representation of how the subject bifunctional molecules inhibit protein—protein interactions in a manner analogous to the way antibodies block such interactions.

The bifunctional inhibitor molecule of the present invention is a non-naturally occurring or synthetic compound that includes a target protein ligand and blocking protein ligand, where these two moieties are optionally joined by a linking group. The bifunctional inhibitor molecule is further characterized in that the target protein ligand and the blocking protein ligand are different, such that the bifunctional molecule may be viewed as a heterodimeric compound produced by the joining of two different moieties. In many embodiments, the blocking protein ligand and the target protein ligand are chosen such that the corresponding target protein and blocking protein do not naturally associate with each other to produce a biological effect. The bifunctional inhibitor molecules are also capable of simultaneously binding their corresponding target and blocking proteins to form a tripartite complex, where the tripartite complex inhibits the binding of the target protein to a second binding protein. See FIG. 1. In forming the tripartite complex, the target protein ligand may bind to a site of the target protein that is the same as the site that is bound by the second binding protein. Alternatively, the target protein ligand may bind to a site of the target protein that is different from the site that is bound by the second binding protein, i.e. the second binding protein binding site of the target protein.

An important feature of the subject molecules is that they are small. As such, the molecular weight of the subject bifunctional inhibitor molecules is generally at least about 100 D, usually at least about 400 D and more usually at least about 500 D, and may be as great as 2000 D or greater, but usually does not exceed about 5000 D.

Bifunctional molecules are generally described by the formula:

wherein

X is a target protein ligand;

L is bond or linking group; and

Z is a blocking protein ligand; with the proviso that X and Z are different.

Target Protein Ligand: X

The target protein ligand X may be any molecule, as well as a binding portion or fragment thereof, that is capable of specifically binding to the target protein of the protein pair of the protein—protein interaction whose inhibition is desired. Generally, X is a small organic molecule that is capable of binding to the target of interest. As X has a low molecular weight, it generally has a molecular weight of at least about 50 D, usually at least about 100 D, where the molecular weight may be as high as 500 D or higher, but will usually not exceed about 2000 D.

The target protein ligand X is capable of interacting with a target protein in the host into which the bifunctional inhibitor molecule is administered during practice of the subject methods. The target protein may be a number of different types of naturally occurring proteins, where targets of interest include both intracellular and extracellular targets proteins. As mentioned above, the target protein is a first member of the pair of proteins whose interaction is to be inhibited in the subject methods. Specific proteinaceous targets of interest include, without limitation, enzymes, e.g. kinases, phosphatases, reductases, cyclooxygenases, proteases and the like, targets comprising domains involved in protein—protein interactions, such as the SH2, SH3, PTB and PDZ domains, structural proteins, e.g. actin, tubulin, etc., membrane receptors, immunoglobulins, e.g. IgE, cell adhesion receptors, such as integrins, etc, ion channels, transmembrane pumps, transcription factors, signaling proteins, and the like.

The X moiety of the subject bifunctional inhibitor molecules are therefore chosen in view of the target protein of the target protein—protein interaction or binding event. As such, the X moiety may be a number of different ligands, depending on the particular endogenous blocking protein to which it is intended to bind. In many preferred embodiments, the X moiety has an affinity for its target protein of at least about $10^{-4}$ M, usually at least about $10^{-6}$ molar and more usually at least about $10^{-8}$ M, where in many embodiments the X moiety has an affinity for its target protein of between about $10^{-9}$ and $10^{-12}$ M. In certain embodiments, the X moiety portion of the bifunctional inhibitor molecule is also specific for the target protein in the context of its binding activity when present in the bifunctional inhibitor molecule, in that it does not significantly bind or substantially affect non-target proteins when it is present in the bifunctional inhibitor molecule.

The target protein ligand of the bifunctional inhibitor compounds includes one or more functional groups necessary for structural interaction with the target, e.g. groups necessary for hydrophobic, hydrophilic, electrostatic or even covalent interactions, depending on the particular target protein ligand and its intended target. Specifically, the target protein ligand includes functional groups necessary for structural interaction with proteins, such as hydrogen bonding, hydrophobic—hydrophobic interactions, electrostatic interactions, etc., and will typically include at least an amine, amide, sulfhydryl, carbonyl, hydroxyl or carboxyl group, preferably at least two of the functional chemical groups. As described in greater detail below, the target protein ligand will also comprise a region that may be modified and/or participate in covalent linkage to the other components of the bifunctional inhibitor molecule, such as the blocking protein ligand or linker, without substantially adversely affecting the target protein ligand's ability to bind to its target.

The target protein ligands often comprise cyclical carbon or heterocyclic structures and/or aromatic or polyaromatic structures substituted with one or more of the above functional groups. Also of interest as target protein ligands are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The target protein ligand of the bifunctional molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the target protein ligand may be obtained from a library of naturally occurring or synthetic molecules, including a library of compounds produced through combinatorial means, i.e. a compound diversity combinatorial library. When obtained from such libraries, the target protein ligand employed will have demonstrated an affinity for its protein target in an appropriate screening assay for the activity. Combinatorial libraries, as well as methods for the production and screening, are known in the art and described in U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Blocking Protein Ligand: Z

Z is a ligand for a blocking protein present in the host into which the bifunctional inhibitor molecule is to be administered. The blocking protein ligand of the subject bifunctional inhibitor molecules binds to a specific blocking protein present in the host. In many embodiments, the binding interaction between the blocking protein and the blocking protein ligand is non-covalent, such that no covalent bonds are produced between the bifunctional molecule and the blocking protein upon binding of the two entities. The blocking protein ligand (Z) has a low molecular weight—it generally has a molecular weight of at least about 50 D, usually at least about 100 D, where the molecular weight may be as high as 500 D or higher, but will usually not exceed about 2000 D. In certain embodiments, the blocking protein ligand, in the context of the bifunctional molecule, has substantially no pharmacological activity at its effective concentration beyond binding to the blocking protein, i.e. it does not directly cause a blocking protein-mediated pharmacological event to occur upon binding at its effective concentration to the blocking protein, where a blocking protein-mediated pharmacological event is a pharmacologically relevant event which is directly modulated by the blocking protein in the absence of the subject bifunctional molecules. By "pharmacologic activity" is meant an activity that modulates or alters a biological process so as to result in a phenotypic change, e.g. cell death, cell proliferation etc. As used herein, pharmacological event is an event that is distinct from a biochemical event (e.g. inhibition a prolyl isomerase activity) or a biological event (e.g. inducement of a cell to express new genes). In other certain embodiments, the blocking protein ligand may have some pharmacological activity, where this pharmacological activity does not adversely effect the host to the extent that the therapy in which the bifunctional molecule is employed places the host in a worst condition than prior to the therapy. In other words, pharmacological activity in the blocking protein ligand may be tolerated in these embodiments to the extent that any consequences of such activity, if any, are outweighed by the benefits provided by the bifunctional molecule.

The blocking protein to which the ligand of the bifunctional inhibitor molecule binds may be any protein that is present in the host at the time the bifunctional molecule is introduced to the host, i.e. the blocking protein is endogenous to the host. The blocking protein may or may not have one or more modified residues, e.g. residues that are glycosylated, such that the blocking protein may or may not be a glycoprotein. Furthermore, the blocking protein that is recruited by the bifunctional molecule may or may not be part of a complex or structure of a plurality of biological molecules, e.g. lipids, where such complexes or structures may include lipoproteins, lipid bilayers, and the like. However, in many embodiments, the blocking protein that is recruited by the blocking protein ligand of the bifunctional molecule will be by itself, i.e. it will not be part of a larger structure of a plurality of biological molecules.

Though the blocking protein may be a protein that is not native to the host but has been introduced at some time prior to introduction of the bifunctional molecule, e.g. through prior administration of the protein or a nucleic acid composition encoding the same, such as through gene therapy, the blocking protein will, in many embodiments, be a protein that is native to and naturally expressed by at least some of the host's cells, i.e. a naturally occurring protein in the host. The blocking protein is a protein that is present in the region of host occupied by the target protein. As such, where the target protein is an intracellular protein, the blocking protein will be an intracellular protein present in the cell comprising the target, typically expressed in the cell comprising the target, i.e. the blocking protein and the target protein are co-expressed in the same cell. Likewise, where the target protein is an extracellular protein, the blocking protein will be an extracellular protein that is found in the vicinity of the target.

Although not a requirement in certain embodiments, in many preferred embodiments the blocking protein is one that is present in the host in sufficient quantities such that, upon binding of at least a portion of blocking protein present in the host to the bifunctional molecule, adverse pharmacological effects do not occur. In other words, the blocking protein in these preferred embodiments is one in which its native and desirable biological activity, if any, is not diminished by an unacceptable amount following binding of the portion of the blocking protein population to the bifunctional molecule. The amount of diminished activity of the blocking protein that is acceptable in a given situation is determined with respect to the condition being treated in view of the benefits of treatment versus the reduction of overall blocking protein activity, if any. In certain situations, a large decrease in overall blocking protein activity may be acceptable, e.g. where the blocking protein activity aggravates the condition being treated.

The size of the blocking protein should be sufficient to sterically inhibit the target protein—protein interaction between the target protein and the second binding protein when a tripartite complex is produced between the target protein, the bifunctional inhibitor molecule and the blocking protein. In many embodiments, the blocking protein is at least about 5 to 10 kD, and may be as high as 1000 to 2000 kD or higher, where the upper limit for the blocking protein is about 300 kD in certain embodiments.

Specific blocking proteins of interest include intracellular and extracellular proteins. Intracellular proteins of interest include: peptidyl-prolyl isomerases, e.g. FKBPs and cyclophilins; ubiquitously expressed molecular chaperones, e.g. Heat Shock Protein 90 (Hsp90); steroid hormone receptors, e.g. estrogen receptors, glucocorticoid receptors, androgen receptors; retinoic acid binding protein, cytoskeletal proteins, such as tubulin and actin; etc.

Of particular interest as intracellular blocking proteins are cis-trans peptidyl-prolyl isomerases which interact with many proteins because of their chaperonin/isomerase activity, e.g. FKBPs and cyclophilins. Peptidyl-prolyl isomerases of interest include FKBPs. A number of different FKBPs are known in the art, and include those described in: Sabatini et al., Mol. Neurobiol. (October 1997) 15:223–239; Marks, Physiol. Rev. (July 1996) 76:631–649; Kay, Biochem J. (March, 1996) 314: 361–385; Braun et al., FASEB J. (January 1995) 9:63–72; Fruman et al, FASEB J. (April 1994) 8:391–400; and Hacker et al., Mol. Microbiol. (November 1993) 10: 445–456. FKBPs of interest include FKBP 12, FKBP 52, FKBP 14.6 (described in U.S. Pat. No. 5,525,523, the disclosure of which is herein incorporated by reference); FKBP 12.6 (described in U.S. Pat. No. 5,457,182 the disclosure of which is herein incorporated by reference); FKBP 13 (described in U.S. Pat. No. 5,498,597, the disclosure of which is herein incorporated by reference); and HCB (described in U.S. Pat. No. 5,196,352 the disclosure of which is herein incorporated by reference); where FKBP 12 and FKBP 52 are of particular interest in certain embodiments as intracellular blocking proteins.

Also of specific interest in certain embodiments as blocking proteins are cyclophilins. A number of cyclophilins are known in the art and are described in Trandinh et al., FASEB J. (December 1992) 6: 3410–3420; Harding et al., Transplantation (August 1988) 46: 29S–35S. Specific cyclophilins of interest as intracellular blocking proteins include cyclophilin A, B, C, D, E, and the like, where cyclophilin A is of particular interest.

Instead of being an intracellular protein, the endogenous blocking protein may be an extracellular or serum protein. Serum blocking proteins of particular interest are those that are relatively abundant in the serum of the host and meet the above criteria for suitable endogenous blocking proteins. By relatively abundant is meant that the concentration of the serum blocking protein is at least about 1 ng/ml, usually at least about 10 µg/ml and more usually at least about 15 µg/ml. Specific serum proteins of interest as blocking proteins include: albumin, Vitamin A binding proteins and Vitamin D binding proteins, β-2 macroglobulin, with albumin being a particularly preferred blocking protein.

The Z moiety of the subject bifunctional inhibitor molecules will therefore be chosen in view of the endogenous blocking protein that is to be recruited to produce the tripartite complex that inhibits the target protein—protein interaction or binding event. As such, the Z moiety may be a number of different ligands, depending on the particular endogenous blocking protein to which it is intended to bind. In many preferred embodiments, the Z moiety has an affinity for its blocking protein of at least about $10^{-4}$ M, usually at least about $10^{-6}$ molar and more usually at least about $10^{-8}$ M, where in many embodiments the Z moiety has an affinity for its blocking protein of between about $10^{-9}$ and $10^{-12}$ M. The Z moiety portion of the bifunctional molecule should also be specific for the blocking protein in the context of its binding activity when present in the bifunctional molecule, in that it does not significantly bind or substantially affect non-blocking proteins when it is present in the bifunctional molecule.

Representative ligands capable of serving as the Z moiety of the bifunctional molecule include ligands for intracellular proteins, such as: peptidyl-prolyl isomerase ligands, e.g. FK506, rapamycin, cyclosporin A and the like; Hsp90 ligands, e.g. geldanamycin; steroid hormone receptor ligands, e.g. naturally occurring steroid hormones, such as estrogen, progestin, testosterone, and the like, as well as synthetic derivatives and mimetics thereof, particularly those which bind with high specificity and affinity but do not activate their respective receptors; small molecules that bind to cytoskeletal proteins, e.g. antimitotic agents, such as taxanes, colchicine, colcemid, nocadozole, vinblastine, and vincristine, actin binding agents, such as cytochalasin, latrunculin, phalloidin, and the like.

As mentioned above, the preferred intracellular blocking proteins in many embodiments of the subject invention are members of the peptidyl-prolyl isomerase family, particularly the FKBP and cyclophilin subsets of this family. Where peptidyl-prolyl isomerase blocking proteins are employed, the bifunctional molecule/peptidyl-prolyl isomerase complex will preferably not substantially bind to the natural peptidyl-prolyl isomerase/ligand target calcineurin so as to result in significant immunosuppression. A variety of ligands are known that bind to FKBPs and may be used in the subject invention. The ligands should specifically bind to an FKBP and have an affinity for the FKBP that is between about $10^{-6}$ and $10^{-10}$ M. Of interest are both naturally occurring FKBP ligands, including FK506 and rapamycin. Also of interest are synthetic FKBP ligands, including those described in U.S. Pat. Nos. 5,665,774; 5,622,970; 5,516, 797; 5,614,547; and 5,403,833, the disclosures of which are herein incorporated by reference.

Also of interest are cyclophilin ligands, where such ligands should specifically bind to cyclophilin with an affinity that is between about $10^{-6}$ and $10^{-9}$ M. A variety of ligands that bind to cyclophilins are also known, where such ligands include the naturally occurring cyclosporins, such as cyclosporin A, as well as synthetic derivatives and mimetics thereof, including those described in U.S. Pat. Nos. 5,401, 649; 5,318,901; 5,236,899; 5,227,467; 5,214,130; 5,122, 511; 5,116,816; 5,089,390; 5,079,341; 5,017,597; 4,940, 719; 4,914,188; 4,885,276; 4,798,823; 4,771,122; 4,703, 033; 4,554,351; 4,396,542; 4,289,851; 4,288,431; 4,220,61 and 4,210,581, the disclosures of which are herein incorporated by reference.

Representative ligands for use as the Z moiety in the bifunctional molecule also include ligands that bind to extracellular blocking proteins. Such ligands should specifically bind to their respective blocking protein with an affinity of at least about $10^{-4}$ M. Ligands of interest for use in binding to extracellular blocking proteins include: albumin ligands, such as arachidonate, bilirubin, hemin, aspirin, ibuprofen, para-amino salicylic acid, myristylate, plamitate, linoleate, warfarin etc.; Vitamin A and derivatives thereof, Vitamin D and derivatives thereof, and the like.

Linking Moiety: L

The Z and X moieties of the bifunctional molecule are joined together through linking moiety L, where L may be either a bond or a linking group. Where linking groups are employed, such groups are chosen to provide for covalent attachment of the two ligand moieties through the linking group, as well as the desired structural relationship of the bifunctional molecule with respect to its intended blocking protein. Linking groups of interest may vary widely depending on the nature of the target and blocking ligand moieties. The linking group, when present, should preferably be biologically inert. Appropriate linkers can be readily identified by those of skill in the art using screening assays which evaluate the ability of the candidate bifunctional inhibitor to form a tripartite complex that inhibits the target protein—protein interaction or binding event. A variety of linking groups are known to those of skill in the art and find use in the subject bifunctional molecules. The linker groups should be sufficiently small so as to provide a bifunctional molecule having the overall size characteristics as described above, the size of the linker group, when present, is generally at least about 50 daltons, usually at least about 100 daltons and may be as large as 1000 daltons or larger, but generally will not exceed about 500 daltons and usually will not exceed about 300 daltons. Generally, such linkers will comprise a spacer group terminated at either end with a reactive functionality capable of covalently bonding to the target protein ligand or blocking protein ligand moieties. Spacer groups of interest possibly include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject bifunctional molecules include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl[4-azidophenyl]-1,3'-dithiopropionate, N-succinimidyl[4-iodoacetyl] aminobenzoate, glutaraldehyde, and succinimidyl 4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

Methods of Making Bifunctional Molecules

The bifunctional molecules of the subject invention may be prepared using any convenient methodology. As indicated above, the bifunctional inhibitor molecule is one that inhibits a target protein—protein interaction or binding event between a target protein and a second binding protein. Generally, a ligand that specifically binds to the target protein is first identified. The ligand may be a previously identified molecule or compound having the desired target binding activity, or one that has been newly discovered using one or more compound discovery techniques. The bifunctional inhibitor molecule is then generally produced from the target protein ligand using a rational or combinatorial approach.

In a rational approach, the bifunctional inhibitor molecules are constructed from their individual components, e.g. target ligand, protein ligand and optional linker. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the bifunctional molecule include: hydroxy, sulfhydryl, amino, and the like. The particular portion of the different components that are modified to provide for covalent linkage will be chosen so as not to substantially adversely interfere with that components desired binding activity, e.g. for the target protein ligand, a region that does not affect the target binding activity will be modified, such that a sufficient amount of the desired target protein binding activity is preserved. Where necessary and/or desired, certain moieties on the components may be protected using blocking groups, as is known in the art, see, e.g. Green & Wuts, Protective Groups in Organic Synthesis (John Wiley & Sons) (1991).

The above component approach to production of the bifunctional inhibitor molecule is best suited for situations where the crystal structures of the blocking protein, blocking protein ligand, target protein ligand and target protein are known, such that molecular modeling can be used to determine the optimal linker size, if any, to be employed to join the different components.

Alternatively, the bifunctional inhibitor molecule can be produced using combinatorial methods to produce large libraries of potential bifunctional molecules which may then be screened for identification of a bifunctional molecule with the desired binding affinity and/or specificity. Methods for producing and screening combinatorial libraries of molecules include U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Alternatively, the bifunctional molecule may be produced using medicinal chemistry and known structure-activity relationships for the blocking protein ligand and the target protein ligand. In particular, this approach will provide insight as to where to join the two moieties to the linker.

Screening Bifunctional Compounds

The resultant bifunctional inhibitor molecules are then screened for those molecules exhibit the desired inhibitory activity with respect to the target protein—protein interaction or binding event between the target protein and a second binding protein. Screening of such activity may be accomplished using any convenient protocol. For example, in vitro binding assays can be employed in which the occurrence of the target binding event in the presence and absence of blocking protein and the candidate bifunctional inhibitor compound is evaluated. In such assays, the occurrence of the binding event in the presence of both the blocking protein and the inhibitor is indicative of a lack of inhibitory activity in the candidate bifunctional molecule, while the absence of a binding event in the presence of both blocking protein and candidate bifunctional molecule indicates that the candidate bifunctional molecule possesses the desired inhibitory effect. By comparison to appropriate controls, e.g. evaluation in the absence of candidate bifunctional inhibitor and/or blocking protein, bifunctional inhibitor molecules that exhibit the desired inhibitory activity are identified. In the above described screening assays, one or of the components may be bound to solid support, labeled reagents for the detection of binding events may be employed, etc., as may be required by the particular format employed and is known by those of skill in the art. A candidate bifunctional inhibitor molecule will generally be considered to have inhibitory activity with respect to a given target protein—protein interaction if the amount of target protein—protein binding under physiological conditions in the presence of the bifunctional inhibitor is decreased by at least about 2-fold, usually at least about 4-fold and more usually at least about 10-fold as compared to a control in which the bifunctional inhibitor molecule is not present.

Methods of Making Bifunctional Molecules for Peptidyl-Prolyl Isomerase Blocking Proteins As mentioned above, one class of preferred embodiments of the subject invention are those embodiments in which the bifunctional molecules specifically bind to endogenous peptidyl-prolyl isomerase blocking proteins present in the host into which the bifunctional molecule is introduced. Thus, bifunctional inhibitor molecules of interest include those in which the endogenous blocking protein is either an FKBP or a cyclophilin.

In preparing bifunctional molecules from FK506, a suitable attachment site on the FK506 structure is identified, modified as necessary, and then covalently attached to the linker or target protein ligand moiety. The structure of FK506 (also known as tacrolimus) is:

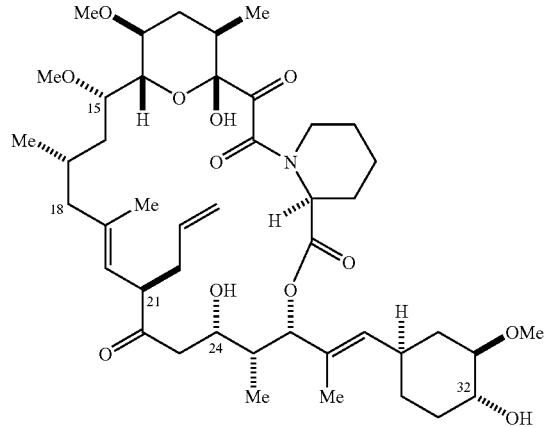

The site to which the linker/target ligand moiety is covalently attached is one that, upon covalent attachment, does not ablate the affinity and/or specificity of FK506 for its FKBP blocking protein, e.g. FKBP 12 or FKBP 52. As such, positions suitable for use as covalent linkage sites include atoms located between carbon 15 and carbon 25 and the substituents attached to these atoms. For example, oxidation of the allyl group or oxidation of the carbon 18 methylene group; modification of the carbon 22 ketone or the carbon 24 hydroxyl group or alkylation at carbon 21 or carbon 23; as well as the secondary hydroxyl group located on the cyclohexyl ring (carbon 32); are potential specific covalent linkage sites.

With FK506, depending on the target protein ligand and/or linker to be attached, it may be desirable to introduce one or more functional moieties onto the FK506 structure. Functional moieties of interest that may be introduced include: hydroxyl groups, amino groups, carboxyl groups, aldehydes, carbonates, carbamates, azides, thiols, and esters, etc. Such groups may be introduced using known protocols, such as oxidation reactions, reduction reactions, cleavage reactions and the like, with or without the use of one or more blocking groups to prevent unwanted side reactions.

In some instances, it is desirable to covalently attach the target protein ligand directly to FK506, often activated FK506. In such instances, the reactive functional group(s) introduced onto the FK506 structure will depend primarily on the nature of the target protein ligand to be attached. Thus, for peptidic target protein ligands, specific pairings of interest include: FK506 carbonates for reacting with amino groups of peptides; FK506 carboxylic acids for reacting with amino groups of peptides; FK506 amines for reacting with carboxylic acid groups of peptides; FK506 maleimide for reacting with thiol groups of peptides; and the like. Alternatively, where the ligand moiety is a steroid, potential pairings of interest include: FK506 N-hydroxysuccinimidyl carbonate and partner amine; FK506 aldehyde and partner amine; FK506 aldehyde and partner hydrazide; FK506 hydroxy group and partner carboxylic acid OR alkyl halide; FK506 thiol and partner maleimide and the like.

Following introduction of the reactive functional group(s) onto the FK506 structure, the activated FK506 is then combined with the ligand moiety/linker under conditions sufficient for covalent bonding to occur.

Another embodiment of particular interest are bifunctional molecules of cyclosporin A or analogs thereof. The structure of cyclosporin A is:

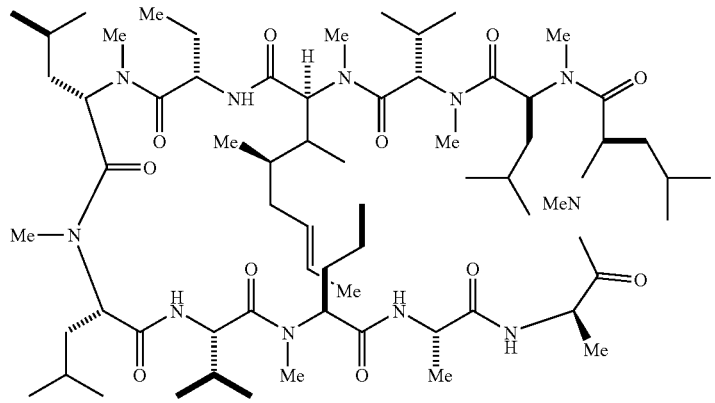

As with the FK506 bifunctional molecules, the cyclosporin A will be conjugated to the target protein ligand in a manner such that cyclosporin A does not substantially lose its affinity for cyclophilin. Preferred positions on the cyclosporin A structure that may serve as covalent linkage sites include: residues 4, 5, 6, 7, 8; while less preferred but still possible residues include: 1, 2, 3, 9, 10 and 11. Where necessary, reactive functionalities may be introduced onto the cyclosporin structure, where such functionalities include: hydroxyl groups, amino groups, carboxyl groups, aldehydes, carbonates, carbamates, azides, thiols, and esters, etc., with the particular functionality of interest being chosen with respect to the specific linker or target protein ligand to be attached.

Methods of Use, Pharmaceutical Preparations and Kits

The subject bifunctional inhibitor molecules find use in methods of inhibiting protein—protein interactions between a first target protein and a second binding protein. This "second binding protein" can also be called an "effector protein," meaning that binding of the target protein to the effector protein is responsible for a biological/physiological response the blockage or inhibition of which is desired with the bifunctional molecules. The target protein—protein interaction or binding event may be one that occurs in vitro or in vivo, but in many preferred embodiments is one that occurs in vivo, in that it occurs in a living organism or host. By inhibiting protein—protein interactions is meant that the presence of the subject bifunctional inhibitor molecules reduces the amount of binding between the first target protein and the second binding protein, generally by at least about 2-fold, usually by at least about 4-fold and more usually by at least about 10-fold, where in certain cases the target protein-effector protein interaction between the target protein and the second binding protein is completely inhibited, i.e. the binding event does not occur. The subject bifunctional compounds inhibit the target binding event between the target protein and the second binding protein by forming a tripartite complex that includes the target protein, the bifunctional molecule and the blocking protein, where the blocking protein member of the tripartite complex inhibits or prevents binding of the second binding protein to the target protein. As such, the subject methods can also be viewed as methods of producing tripartite complexes that inhibit or prevent the binding of a target protein to a second binding protein.

In the methods of the subject invention, an effective amount of the bifunctional molecule is administered to the host, where "effective amount" means a dosage sufficient to produce the desired result, e.g. an improvement in a disease condition or the symptoms associated therewith which are mediated at some point by the protein/protein interaction that is inhibited by the bifunctional condition. The bifunctional molecule may be administered to the host using any convenient means capable of producing the desired result. Thus, the bifunctional molecule can be incorporated into a variety of formulations for therapeutic administration. More particularly, the bifunctional molecule of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the bifunctional molecule can be achieved in various ways, including oral, buccal, rectal, parenteral, intraperitoneal, intradermal, transdermal, intracheal, etc., administration. In pharmaceutical dosage forms, the bifunctional molecule may be administered alone or in combination with other pharmaceutically active compounds. The following methods and excipients are merely exemplary and are in no way limiting.

For oral preparations, the bifunctional molecules can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The bifunctional molecules can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The bifunctional molecules can be utilized in aerosol formulation to be administered via inhalation. The compounds of the present invention can be formulated into pressurized acceptable propellants such as dichlorodifluoromethane, propane, nitrogen and the like.

Furthermore, the bifunctional molecules can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions which are mediated, at least in part, by the occurrence of protein—protein interactions between a target protein and a second binding protein. The specific disease conditions treatable by with the subject bifunctional compounds are varied. Thus, disease conditions include cellular proliferative diseases, such as neoplastic diseases, autoimmune diseases, cardiovascular diseases, hormonal abnormality diseases, infectious diseases, and the like.

By treatment is meant at least an amelioration of at least one of the symptoms associated with the disease condition afflicting the host, where amelioration is used in a broad sense to refer to at least a reduction in the magnitude of a parameter, e.g. symptom, associated with the pathological condition being treated, such as inflammation and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the bifunctional molecule, usually in oral or injectable doses and often in a storage stable formulation, are provided. In such kits, in addition to the containers containing the unit doses will be an informational package insert describing the use and attendant benefits of the bifunctional molecules in treating pathological condition of interest. Preferred compounds and unit doses are those described herein above.

The following examples are offered by way of illustration and not by way of limitation.

EXPERIMENTAL

I. Introduction

The NFAT transcription factor plays an important role in the activation of T-lymphocytes. A molecule that inhibits the NFAT transcription factor would be a potent immunosuppressant drug. The regulation of NFAT involves two important events: first, NFAT has to be dephosphorylated which unveils a nuclear translocation signal. Second, the nuclear translocation machinery has to bind to the nuclear translocation signal to move the protein from the cytoplasm into the nucleus. The critical phosphorylation sites and the nuclear localization signal are found in the N-terminus of NFAT.

II. Assay Design and Results

Figure 2:
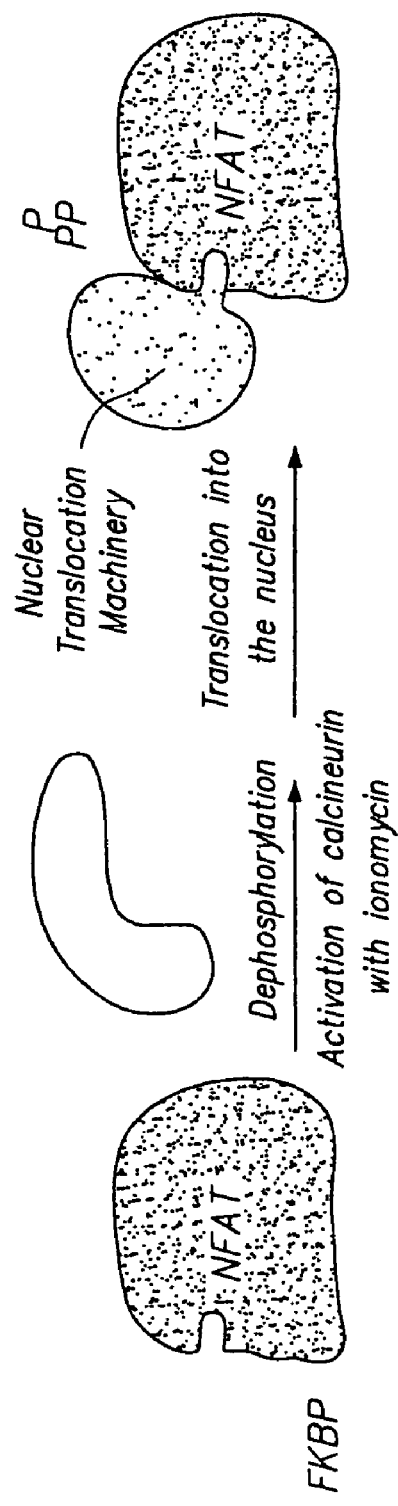
FIG. 2 provides a representation of how NFAT translocates into the nucleus after activation of calcineurin with ionomycin.

Using the blocker protein approach to interfere with dephosphorylation or translocation of NFAT requires having a ligand in the N-terminus of NFAT that, by itself, does not cause any inactivation of the protein. Such a ligand has not been identified, yet, because so far such ligands have been of no biological interest. In order to overcome this problem, a binding site was created for a ligand at the N-terminus of NFAT by fusing it to an FKBP protein which can bind the small molecule rapamycin. The resulting FKBP-NFAT fusion protein is regulated normally. After transfection of the cDNA into COS cells, the expressed protein is localized in the cytoplasm. When the cells are treated with ionomycin, FKBP-NFAT translocates into the nucleus. Ionomycin is an ionophore which leads to an increase in intracellular calcium. As a result, the phosphatase calcineurin is activated. Calcineurin dephosphorylates FKBP-NFAT and the nuclear translocation machinery translocates the fusion protein into the nucleus as it would NFAT (FIG. 2).

Figure 3:
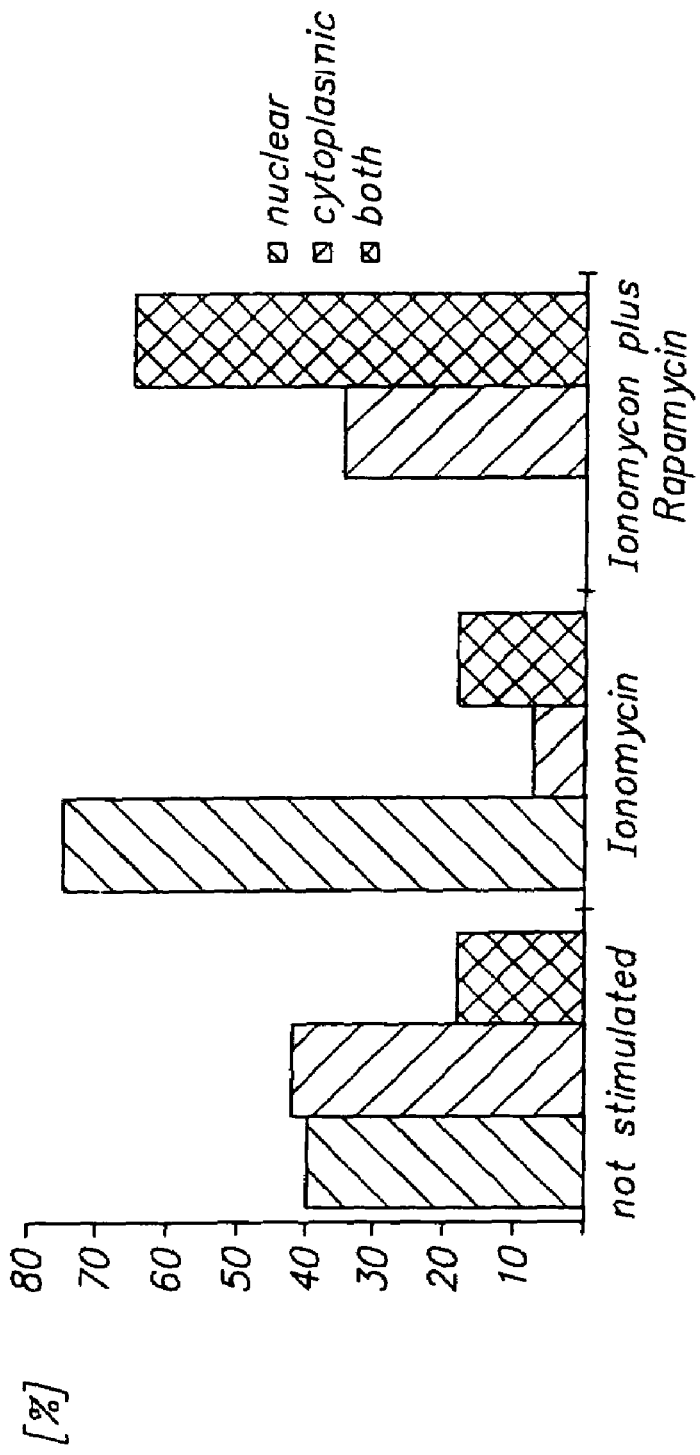
FIG. 3 provides a graphical representation of assay results which demonstrate that binding of FRB to FKBP-NFAT with rapamycin abolishes translocation into the nucleus.
Figure 4:
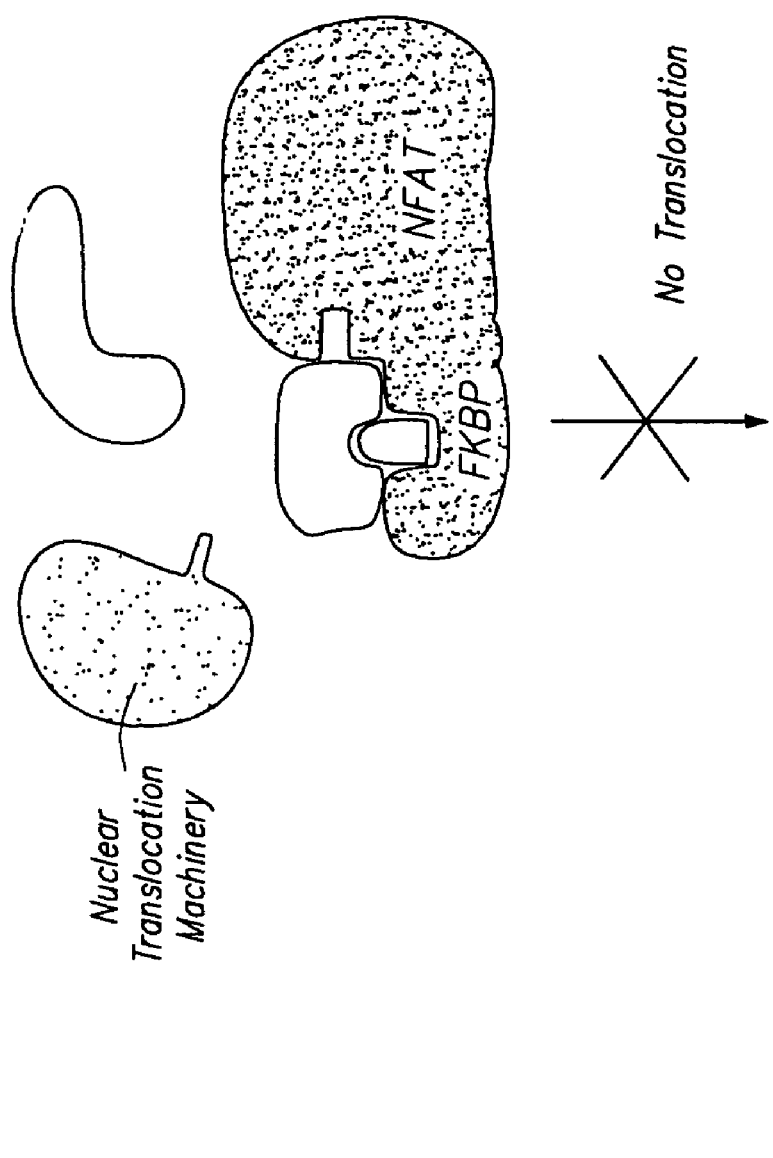
FIG. 4 provides a schematic representation of how steric blockage prevents access of regulatory proteins to NFAT.

Like FK506 and cyclosporin, rapamycin is a bifunctional molecule. It binds FKBP and the protein kinase FRAP simultaneously. FRAP is a large protein but within this large protein the rapamycin binding site maps to a small 87 amino acid domain. This domain can be coexpressed in cells together with FKBP-NFAT. In the absence of rapamycin, the FRB domain and FKBP do not interact and FKBP-NFAT is translocated normally after stimulation with ionomycin. However, when rapamycin is added, the molecule binds FKBP and the FKBP-rapamycin complex recruits and binds FRB. This localizes the FRB protein domain at the N-terminus of NFAT. When ionomycin is now used to trigger the translocation of FKBP-NFAT, the fusion protein remains in the cytoplasm (FIG. 3). The FRB domain bound at the N-terminus of NFAT establishes a block that prevents the interaction of NFAT with calcineurin or with the nuclear translocation machinery (FIG. 4). These results demonstrate that the mode of action of FK506 and cyclosporin is generalizable: a bifunctional molecule can be used to recruit an endogenous blocking molecule to any given drug target so that a steric block is established which prevents other proteins from interacting with the target.

It is evident from the above results and discussion that the subject invention provides a powerful new tool for inhibiting protein—protein interactions. Specifically, the subject invention provides small molecule therapeutics which are capable of inhibiting both extracellular and intracellular protein—protein interactions. As such, the subject methods and compositions provide for new treatment protocols for a variety of disease and other conditions. Accordingly, the invention represents an important advancement in pharmacological science.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of inhibiting a binding event between a target protein (T) and a binding protein (P), comprising:
   administering to a cell in vitro an effective amount of a non-naturally occurring bifunctional inhibitor molecule (I) of less than 5000 daltons consisting essentially of:
   (a) a target protein ligand that specifically binds to a target protein (T); and (b) a blocking protein ligand that specifically binds to a blocking protein (B), wherein said target protein ligand and said blocking protein ligand are covalently bonded to each other, optionally through a linking group wherein said target protein ligand is NFAT and said blocking protein ligand is FKBP;

in order to non-covalently bind the target protein (T) and the blocking protein (B) to produce a tripartite complex (T—I—B) that prevents access of the binding protein (P) to the target protein (T).

2. The method according to claim 1, wherein said bifunctional inhibitor molecule comprises a linking group.

3. The method according to claim 1, wherein said bifunctional inhibitor molecule (I) binds to a site of said target protein that is also bound by said binding protein (P).

4. The method according to claim 1, wherein said bifunctional inhibitor molecule (I) binds to a site of said target protein (T) that is not bound by said binding protein (P).

5. The method according to claim 1, wherein said tripartite complex is produced intracellularly.

6. The method according to claim 1, wherein said tripartite complex is produced extracellularly.

7. The method according to claim 1, wherein said blocking protein (B) is endogenous to said cells.

8. The method according to claim 7, wherein said blocking protein (B) is selected from the group consisting of: peptidyl-prolyl isomerases, Hsp90 (Heat shock protein 90), steroid hormone receptors, cytoskeletal proteins, albumin and vitamin receptors.

9. A method of inhibiting a binding event between a target protein (T) and a binding protein (P), comprising:

administering to a cell in vitro an effective amount of a non-naturally occurring bifunctional inhibitor molecule (I) of less than 5000 daltons consisting essentially of:

(a) a target protein ligand that specifically binds to a target protein (T) with a binding affinity of at least about $10^{-4}$ M; and (b) a blocking protein ligand that specifically binds to a blocking protein (B), wherein said blocking protein ligand is a peptidyl-prolyl isomerase ligand, wherein said target protein ligand and said blocking protein ligand are covalently bonded to each other, optionally through a linking group wherein said target protein ligand is NFAT and said blocking protein ligand is FKBP;

in order to non-covalently bind the target protein (T) and the blocking protein (B) to produce a tripartite complex (T—I—B) that prevents access of the binding protein (P) to the target protein (T).

10. The method according to claim 9, wherein said bifunctional inhibitor molecule comprises a linking group.

11. The method according to claim 9, wherein said bifunctional inhibitor molecule (I) binds to a site of said target protein that is also bound by said binding protein (P).

12. The method according to claim 9, wherein said bifunctional inhibitor molecule (I) binds to a site of said target protein (T) that is not bound by said binding protein (P).

13. The method according to claim 9, wherein said tripartite complex is produced intracellularly.

14. The method according to claim 9, wherein said blocking protein (B) is endogenous to said cells.

15. The method according to claim 1, wherein said blocking protein ligand is a peptidyl-prolyl isomerase ligand.

16. The method according to claim 1, wherein said ligand for an FKBP is selected from the group consisting of FK506 and rapamycin.

17. The method according to claim 9, wherein said ligand for an FKBP is selected from the group consisting of FK506 and rapamycin.

* * * * *

UNITED STATES PATENT AND TRADEMARK OFFICE
CERTIFICATE OF CORRECTION

PATENT NO. : 7,220,552 B1 Page 1 of 1
APPLICATION NO. : 09/716054
DATED : May 22, 2007
INVENTOR(S) : Gerald R. Crabtree et al.

It is certified that error appears in the above-identified patent and that said Letters Patent is hereby corrected as shown below:

In The Claims:

- Column 17, Line 6: Please add --a ligand for an-- after the word is.
- Column 17, Line 7: Please add --a ligand for an-- after the word is.
- Column 18, Line 7: Please add --a ligand for an-- after the word is.
- Column 18, Line 8: Please add --a ligand for an-- after the word is.
- Column 18: Please delete claim 15.
- Column 18: Please renumber claim "16" to read as claim --15--.
- Column 18: Please renumber claim "17" to read as claim --16--.

Signed and Sealed this

Twenty-fifth Day of November, 2008

JON W. DUDAS
*Director of the United States Patent and Trademark Office*